United States Patent
Baiko et al.

(10) Patent No.: US 10,449,316 B2
(45) Date of Patent: Oct. 22, 2019

(54) MASK WITH RED MARK ALLEVIATING POCKET

(71) Applicant: KONINKLIJKE PHILIPS N.V., Eindhoven (NL)

(72) Inventors: Robert William Baiko, Pittsburgh, PA (US); Lauren Patricia Chodkowski, Pittsburgh, PA (US); Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 736 days.

(21) Appl. No.: 14/651,867

(22) PCT Filed: Dec. 3, 2013

(86) PCT No.: PCT/IB2013/060586
§ 371 (c)(1),
(2) Date: Jun. 12, 2015

(87) PCT Pub. No.: WO2014/091360
PCT Pub. Date: Jun. 19, 2014

(65) Prior Publication Data
US 2015/0335845 A1    Nov. 26, 2015

Related U.S. Application Data

(60) Provisional application No. 61/736,706, filed on Dec. 13, 2012.

(51) Int. Cl.
*A61M 16/06* (2006.01)

(52) U.S. Cl.
CPC ............... *A61M 16/0622* (2014.02)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS

| 4,665,570 | A | * | 5/1987 | Davis | ............ A61M 16/06 2/428 |
| 5,355,878 | A | * | 10/1994 | Griffiths | ........... A62B 18/025 128/201.23 |

(Continued)

FOREIGN PATENT DOCUMENTS

| DE | 102007042733 | * | 6/2008 | ............ A61M 16/06 |
| EP | 1099452 A2 | * | 5/2001 | ............ A61M 16/06 |
| WO | WO2011003128 A1 | | 1/2011 | |

OTHER PUBLICATIONS

Machine translation of EP 1099452 A2.*
By-hand translation of Genger et al. (EP 1099452 A2).*

*Primary Examiner* — Joseph D. Boecker
(74) *Attorney, Agent, or Firm* — Michael W. Haas (57) ABSTRACT

A patient interface device that overcomes the shortcomings of conventional patient interface devices is provided. One embodiment of the patient interface device provides a cushion for a patient interface device that includes a first end portion structured to contact a portion of a patient's face. The first end portion includes an inner, first surface, an outer, second surface and at least one pocket disposed between the first end portion first surface and the first end portion second surface.

18 Claims, 4 Drawing Sheets

(58) Field of Classification Search
CPC .......... A61M 2016/0661; A62B 18/00; A62B 18/02; A62B 18/025
See application file for complete search history.

(56) References Cited

U.S. PATENT DOCUMENTS

| | | | |
|---|---|---|---|
| 2003/0168063 A1* | 9/2003 | Gambone | A61M 16/06 128/203.16 |
| 2005/0199239 A1* | 9/2005 | Lang | A61M 16/06 128/206.24 |
| 2006/0185675 A1 | 8/2006 | Colin | |
| 2007/0107733 A1 | 5/2007 | Ho | |
| 2007/0163594 A1 | 7/2007 | Ho | |
| 2007/0215161 A1 | 9/2007 | Frater | |
| 2007/0221227 A1* | 9/2007 | Ho | A61M 16/06 128/206.24 |
| 2008/0006277 A1* | 1/2008 | Worboys | A61M 16/06 128/207.13 |
| 2008/0081114 A1 | 4/2008 | Johanson | |
| 2008/0110464 A1* | 5/2008 | Davidson | A61M 16/06 128/206.26 |
| 2008/0149104 A1 | 6/2008 | Eifler | |
| 2008/0216214 A1 | 9/2008 | Dolby | |
| 2008/0289633 A1 | 11/2008 | Kwok | |
| 2009/0000623 A1* | 1/2009 | Lynch | A61M 16/06 128/206.24 |
| 2009/0044806 A1* | 2/2009 | Burz | A61M 16/06 128/205.25 |
| 2009/0107507 A1 | 4/2009 | Moore | |
| 2009/0139526 A1* | 6/2009 | Melidis | A61M 16/06 128/206.26 |
| 2010/0024811 A1* | 2/2010 | Henry | A61H 9/0078 128/202.16 |
| 2010/0192955 A1 | 8/2010 | Biener | |
| 2010/0294281 A1 | 11/2010 | Ho | |
| 2011/0088699 A1 | 4/2011 | Skipper | |
| 2011/0162654 A1* | 7/2011 | Carroll | A61M 16/06 128/206.21 |
| 2011/0174310 A1* | 7/2011 | Burz | B29C 45/4407 128/206.24 |
| 2011/0186051 A1* | 8/2011 | McAuley | A61M 16/06 128/206.24 |
| 2012/0132208 A1 | 5/2012 | Judson | |
| 2012/0234326 A1* | 9/2012 | Mazzone | A61M 16/06 128/206.26 |
| 2012/0285464 A1* | 11/2012 | Birch | A61B 5/08 128/205.25 |
| 2013/0025589 A1* | 1/2013 | Darvill | A62B 17/04 128/201.25 |
| 2014/0044905 A1* | 2/2014 | Nickol | A61M 16/06 428/35.7 |

* cited by examiner

MASK WITH RED MARK ALLEVIATING POCKET

CROSS-REFERENCE TO RELATED APPLICATIONS

This patent application claims the priority benefit under 35 U.S.C. § 371 of international patent application no. PCT/IB2013/060586, filed Dec. 3, 2013, which claims the priority benefit under 35 U.S.C. § 119(e) of U.S. Provisional Application No. 61/736,706, filed on Dec. 13, 2012, the contents of which are herein incorporated by reference.

BACKGROUND OF THE INVENTION

1. Field of the Invention

The present invention generally relates to a patient interface device for use in a pressure support system that supplies a flow of gas to the airway of a patient, and, in particular, to a patient interface device that includes a cushion with pockets of a low-viscosity medium disposed adjacent a patient's face.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Typically patient interface devices include a mask having a faceplate and a cushion. The cushion is coupled to the faceplate. The cushion contacts the surface of the patient. The mask faceplate and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that in order for the mask to maintain a seal without any undue gas leaks around the periphery of the mask, the mask may be compressed against the patient's face. Over time, the patient's face may become irritated at the point of contact between the cushion and the patient's face.

More specifically, movement, even slight movements, by the patient cause the cushion to rub against the patient's face. That is, shear forces transferred through the mask may cause the inner surface of the cushion to irritate the patient's face. Such irritation may cause red marks to appear on the patient's face. After the mask is removed, the red marks may last minutes or hours. This is a problem as patients do not like having an irritated face nor having red marks on their face.

SUMMARY OF THE INVENTION

Accordingly, it is an object of the present invention to provide a patient interface device that overcomes the shortcomings of conventional patient interface devices. This object is achieved according to one embodiment of the present invention by providing a cushion for a patient interface device, the cushion including a first end portion structured to contact a portion of a patient's face. The first end portion includes an inner, first surface, an outer, second surface and a number of pockets disposed between the first end portion first surface and the first end portion second surface.

It is yet another object of the present invention to provide a patient interface device including a mask with a faceplate and a cushion. The cushion includes a first end portion structured to contact a portion of a patient's face, a second end portion structured to be coupled to the faceplate, a sidewall extending between the first end portion and the second end portion. The first end portion includes a first surface, a second surface and a number of pockets disposed between the first end portion first surface and the first end portion second surface. The cushion second end portion is coupled to the faceplate.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an" and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, "thickness" is taken in a direction generally perpendicular to a surface.

Figure 1:
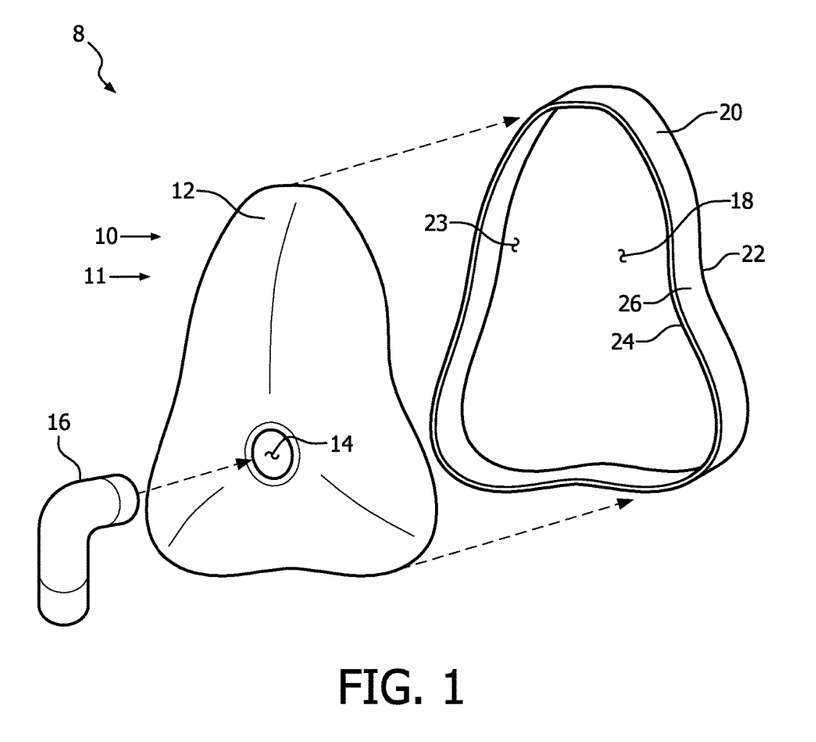
FIG. 1 is an exploded view of a respiratory interface device according to the principles of the present invention
Figure 2:
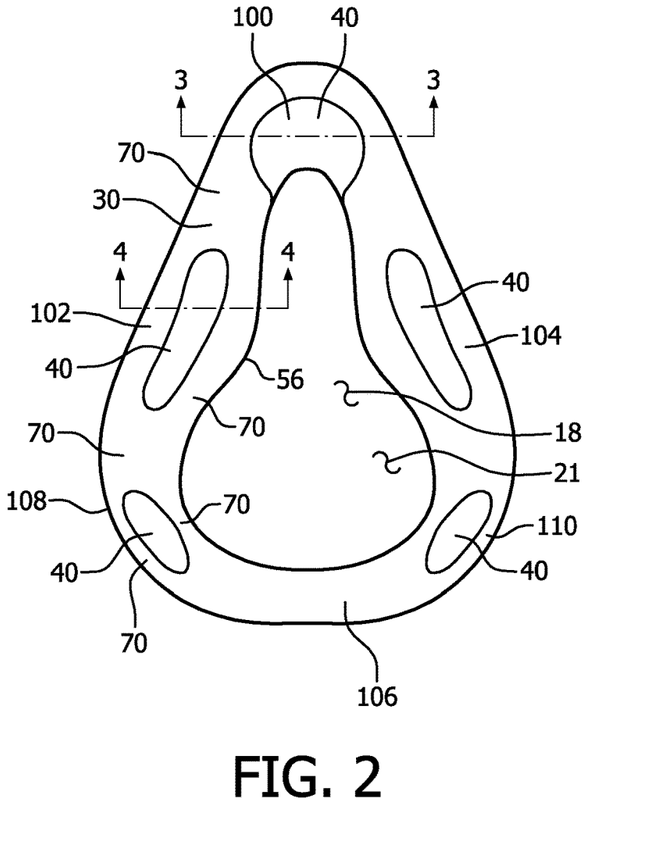
FIG. 2 is a plan view of a cushion first end portion of the respiratory interface device of FIG. 1.

FIG. 1 shows a respiratory interface device 8 according to an exemplary embodiment of the invention. Respiratory interface device 8 includes a respiratory mask 10. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation PAV® device, proportional positive airway pressure (PPAP) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory mask 10 includes a body 11 with a faceplate 12 and a cushion 20, discussed below. In an exemplary embodiment, faceplate 12 is substantially rigid. In an exemplary embodiment, shown in FIG. 1, faceplate 12 is a single piece structured to cover the user's nose. That is, mask 10 has a peripheral contour that is structured to extend over a user's nose and mouth. In this embodiment, body 11 is coextensive with faceplate 12. It is understood that this is an exemplary embodiment and mask 10 may be structured to extend over the user's nose and mouth, just the user's mouth, or just the user's nose. Further, it is understood that faceplate 12 may be made from a soft or flexible material. Faceplate 12 defines lower opening 14. Lower opening 14 can function as a gas inlet.

Gas inlet (lower opening 14) can be coupled to a coupling device 16, such as a swivel conduit, for carrying gas such as air between mask 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from mask 10. Thus, a variety of coupling devices (e.g., with or without swivels on one or both ends, and with or without an exhalation system formed integral to the device) may be substituted for coupling device 16.

Cushion 20 is made from a soft, flexible material such as, but not limited to, silicone PVC, TPE, other plastics, fabrics and cloth. In an exemplary embodiment, cushion 20 is a unitary body. Cushion 20 defines a cavity 18. Cushion 20 includes an inner opening 21 and an outer opening 23. Gas is communicated to cushion cavity 18 via coupling device 16 and outer cushion opening 23. Cushion inner opening 21 is sized and shaped to extend about a patient's nose, mouth, or nose and mouth. Cushion 20 includes a first end portion 22, a second end portion 24, and a sidewall 26. First end portion 22 is structured to contact a portion of a patient's face. First end portion 22 is discussed in detail below. Second end portion 24 is structured to be coupled to faceplate 12. That is, the perimeter of second end portion 24 generally corresponds to the perimeter of faceplate 12 and second end portion 24 is coupled to faceplate 12. Sidewall 26 extends between first end portion 22 and second end portion 24. Thus, sidewall 26 maintains first end portion 22 and second end portion 24 in a spaced relationship. In an exemplary embodiment, sidewall 26 is flexible and allows first end portion 22 and second end portion 24 to shift or move relative to each other while generally maintaining their spacing.

As shown in FIGS. 2-6, first end portion 22 includes a first surface 30 and a second surface 32 (FIGS. 3-6). First end portion first surface 30 is structured to contact a portion of a patient's face. A number of pockets 40 are disposed between first end portion first surface 30 and first end portion second surface 32. Each pocket 40 is filled with a low-viscosity medium 42. In an exemplary embodiment, each pocket 40 is filled with the same low-viscosity medium 42. In an exemplary embodiment, low-viscosity medium 42 is a medium selected from the group including air, oil, silicone fluid, or a gel. Further, low-viscosity medium 42 may be a mixture of low-viscosity mediums. For example, low-viscosity medium 42 may be, but is not limited to, a mixture of air and silicone fluid. In this configuration, shear forces are not transferred through pockets 40.

Figure 4:
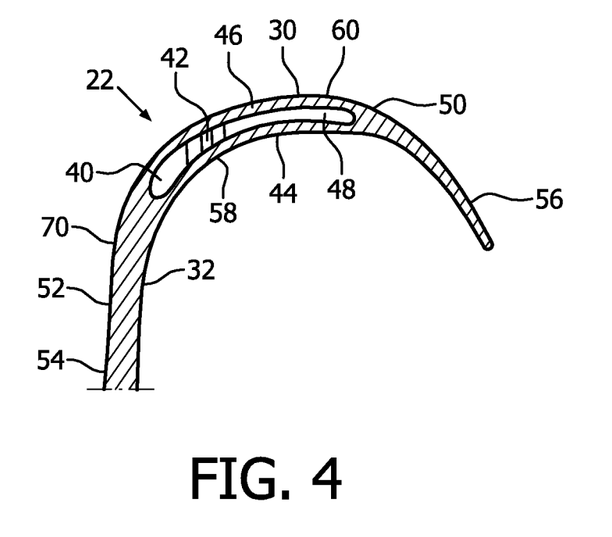
FIG. 4 is a cross-sectional view of another pocket according to according to the principles of the present invention.

In an exemplary embodiment, first end portion 22 has a generally curved cross-section, as shown in FIG. 4. That is, first end portion 22 includes a sealing flap 50 and a perpendicular portion 52. First end portion perpendicular portion 52 is coupled to, and in an exemplary embodiment unitary with, sidewall 26. In an exemplary embodiment, first end portion sealing flap 50 has a generally arcuate cross-section. First end portion sealing flap 50 includes a proximal end 54 and a distal end 56. First end portion sealing flap 50 includes an inner surface 58 and an outer surface 60. First end portion sealing flap inner surface 58 and first end portion sealing flap outer surface 60 are coextensive with first end portion second surface 32 and first end portion first surface 30, respectively. First end portion sealing flap 50 has a thickness, which is the distance between sealing flap inner surface 58 and sealing flap outer surface 60.

Figure 3:
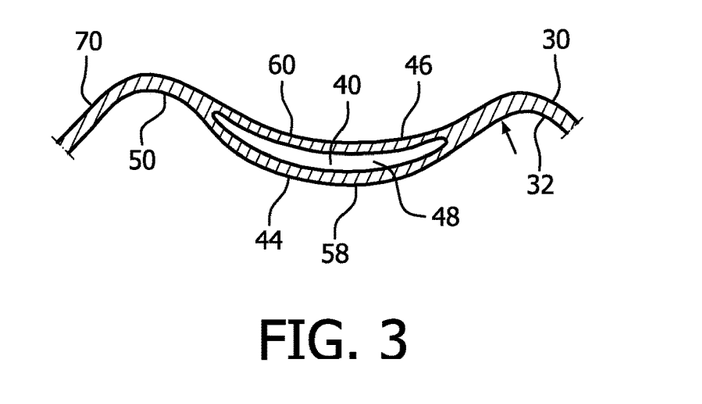
FIG. 3 is a cross-sectional view of a pocket in the cushion portion of the respiratory interface device.

In an exemplary embodiment, shown in FIG. 3, each pocket 40 is incorporated into first end portion sealing flap 50. In this embodiment, each pocket 40 includes an inner wall 44, an outer wall 46, and a plenum 48. Pocket plenum 48 is disposed between pocket inner wall 44 and pocket outer wall 46. As discussed below, the thickness of each pocket 40 includes the thickness of each pocket plenum 48. The pocket 40 is generally thin and, in an exemplary embodiment, is proportional to the wall thickness of cushion 20. For pocket 40 to be effective, pocket 40 thickness will be smaller or equal to the general wall thickness of cushion 20. Thus, in an exemplary embodiment, pocket plenum 48 thickness is around 50% to 90% of the wall thickness of cushion 20.

In a specific exemplary embodiment, which is not limiting on the claims, cushion 20 wall thickness, i.e. the combined thickness of pocket inner wall 44 and pocket outer wall 46 without pocket plenum 48, is between about 0.30 mm and 1.00 mm. Thus, the pocket plenum 48 thickness would be 0.15 mm to 0.50 mm. Medium 42 can slightly inflate pocket plenum 48. In an exemplary embodiment, an inflated pocket plenum 48 will be around 1.5 to 2 times the wall thickness of cushion 20. Thus, in this specific exemplary embodiment, pocket plenum 48 is inflated to have a thickness of between about 0.45 mm to 2.0 mm. Thus, depending upon the inflation of pocket plenum 48, pocket plenum 48 may have a thickness of between about 0.15 mm and 2.0 mm. Further, in this specific exemplary embodiment, the distance between pocket inner wall 44 and pocket outer wall 46 is between about 1.45 mm and 3.0 mm.

In an exemplary embodiment, each pocket 40 is unitary with first end portion sealing flap 50. That is, each pocket 40 may be created by blow molding during the manufacture of cushion 20. Thus, first end portion sealing flap 50 is unitary with pocket inner wall 44 and pocket outer wall 46. It is noted that during blow molding, low-viscosity medium 42 may be placed in each pocket plenum 48.

In an exemplary embodiment as shown in FIG. 1, each pocket 40 is located at a discrete location on first end portion sealing flap 50. That is, first end portion sealing flap 50 includes a number of solid segments 70 in addition to pockets 40. Generally, first end portion sealing flap solid segments 70 are disposed between, and extend about, each pocket 40. That is, the portions of first end portion sealing flap 50 that are not pockets 40 are first end portion sealing flap solid segments 70. Further, the first end portion sealing flap solid segments 70 are unitary with pocket inner wall 44 and pocket outer wall 46.

In an exemplary embodiment shown in FIG. 3, wherein each pocket 40 is incorporated into first end portion sealing flap 50, first end portion sealing flap 50 does not have a generally uniform thickness. That is, first end portion sealing flap solid segments 70 are thinner than pockets 40. If pocket inner wall 44 and pocket outer wall 46 are thinner than first end portion sealing flap solid segments 70, the increased thickness of pockets 40 may be accomplished by inflating pocket plenum 48 so that the total thickness of pocket inner wall 44, pocket plenum 48 and pocket outer wall 46 is greater than the thickness of first end portion sealing flap solid segments 70. Alternatively, pocket inner wall 44 and pocket outer wall 46 may have a thickness the same as or greater than first end portion sealing flap solid segments 70. Thus, the total thickness of pocket inner wall 44, pocket plenum 48 and pocket outer wall 46 is greater than the thickness of first end portion sealing flap solid segments 70. As blow molding is likely to produce a pocket 40 with rounded edges, it is understood that, at the edge of pocket 40, pocket inner wall 44 and pocket outer wall 46 increase in thickness becoming a first end portion sealing flap solid segment 70.

In an exemplary embodiment shown in FIG. 4, wherein each pocket 40 is incorporated into first end portion sealing flap 50, first end portion sealing flap 50 has a generally uniform thickness. That is, first end portion sealing flap solid segments 70 and pockets 40 have a generally uniform thickness. In this exemplary embodiment, pocket inner wall 44 and pocket outer wall 46 are thinner than first end portion sealing flap solid segments 70. Thus, the total thickness of pocket inner wall 44, pocket plenum 48 and pocket outer wall 46 is generally the same as the thickness of first end portion sealing flap solid segments 70. It is understood that, as used herein, the phrase "sealing flap with a generally uniform thickness" does not include the thickness of first end portion sealing flap distal end 56 which may be tapered or rounded.

Figure 5:
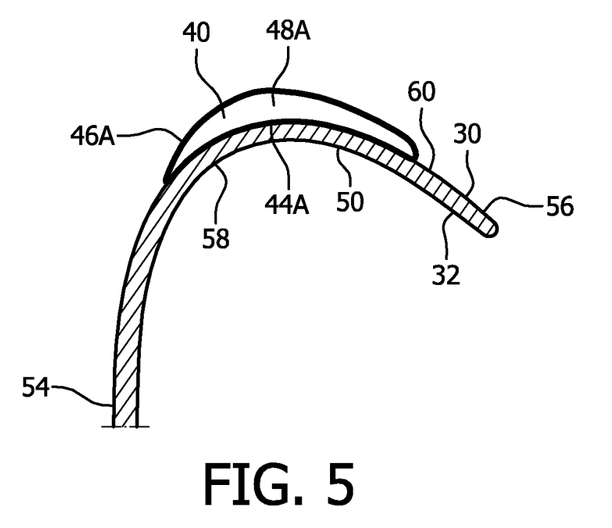
FIG. 5 is a cross-sectional view of an alternate pocket according to the principles of the present invention.

In another exemplary embodiment shown in FIG. 5, each pocket 40 is bonded to first end portion sealing flap 50. In this embodiment, each pocket 40 includes an inner wall 44A, an outer wall 46A, and a plenum 48A. That is, each pocket inner wall 44A and each pocket outer wall 46A are unitary and define an enclosed space that is pocket plenum 48A, or, each pocket inner wall 44A and each pocket outer wall 46A are coupled together about their respective peripheries with pocket plenum 48A disposed between pocket inner wall 44A and pocket outer wall 46A. Thus, each pocket 40 is an individual element. Each pocket 40 is coupled to first end portion sealing flap 50. More specifically, each pocket inner wall 44A is coupled, or directly coupled, to first end portion sealing flap outer surface 60. In this embodiment, each pocket 40 extends outwardly from first end portion sealing flap outer surface 60.

Figure 6:
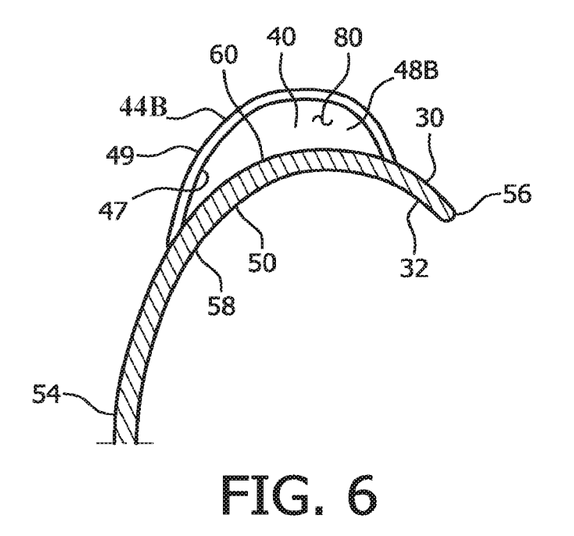
FIG. 6 is a cross-sectional view of another alternate pocket according to the principles of the present invention.

In another exemplary embodiment shown in FIG. 6, each pocket 40 is a single outer wall 44B bonded to first end portion sealing flap 50. That is, each pocket 40 includes a convex outer wall 44B including an inner surface 47 and an outer surface 49. Pocket outer wall inner surface 47 is coupled to first end portion sealing flap outer surface 60. As pocket outer wall 44B is convex, a space 80 is created between the pocket convex wall inner surface 47 and first end portion sealing flap outer surface 60. That is, pocket space 80 is a plenum 48B defined by pocket outer wall inner surface 47 and first end portion sealing flap outer surface 60.

Figure 7:
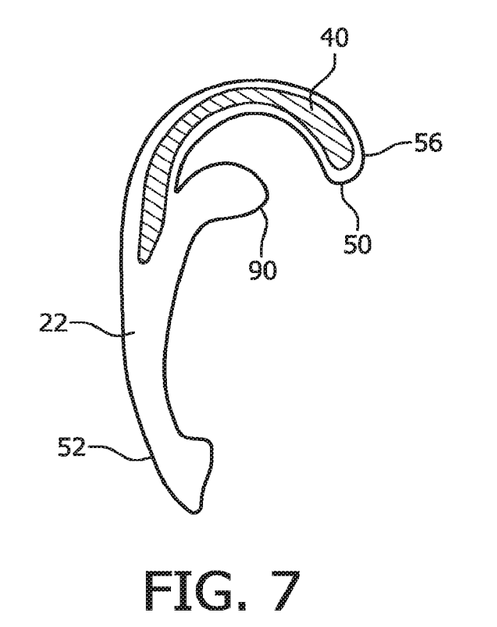
FIG. 7 is a cross-sectional view of an alternate cushion first end portion according to the principles of the present invention.

In an exemplary embodiment, shown in FIG. 7, first end portion 22 includes a support flap 90. Support flap 90 extends from first end portion sealing flap inner surface 58. Support flap 90 at least partially overlays first end portion sealing flap 50.

In an exemplary embodiment, shown in FIG. 1, cushion 20 is generally triangular. In this configuration, first end portion sealing flap 50 includes an apex region 100, a first side region 102, a second side region 104, a bottom region 106, a first transition region 108, and a second transition region 110. Each side region 102, 104 extends from apex region 100. First transition region 108 is disposed between first side region 102 and bottom region 106. Second transition region 110 is disposed between second side region 104 and bottom region 106. Pocket 40 is disposed at one of, and in an exemplary embodiment, each of, apex region 100, first side region 102, second side region 104, first transition region 108, or second transition region 110. In this configuration, and with pockets 40 shaped as described above, shear forces transmitted from faceplate 12 to cushion 20 are reduced, solving the problem of cushions 20 irritating a patient's face.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for a patient interface device, the cushion comprising:
    a first end portion structured to contact a portion of a patient's face;
    the first end portion including:
    an inner, first surface,
    an outer, second surface,
    a sealing flap;
    a number of pockets on the sealing flap, the number of pockets disposed between the first end portion first surface and the first end portion second surface, and
    a number of solid segments, wherein each pocket is located at a discrete location with the solid segments generally disposed about each pocket;
    each pocket includes an inner wall, an outer wall, and a plenum, the plenum disposed between the inner wall and the outer wall;
    wherein the sealing flap solid segments are unitary with each pocket inner wall and each pocket outer wall; and
    wherein the thickness of each sealing flap solid segment is less than the thickness of each pocket.

2. The cushion of claim 1, wherein each pocket is filled with a low-viscosity medium.

3. The cushion of claim 2, wherein the low-viscosity medium is a medium selected from the group including air, oil, silicone fluid, or a gel.

4. The cushion of claim 1, wherein the first end portion includes a support flap, and the first end portion support flap at least partially overlies the first end portion sealing flap.

5. The cushion of claim 1, wherein: the first end portion sealing flap includes an apex region, a first side region, a second side region, a bottom region, a first transition region, and a second transition region, each side region extending from the apex region, the first transition region disposed between the first side region and the bottom region, the second transition region disposed between the second side region and the bottom region; and wherein the discrete location of a pocket is one of the apex region, the first side region, the second side region, the first transition region, or the second transition region.

6. A cushion for a patient interface device, the cushion comprising:
    a first end portion structured to contact a portion of a patient's face;
    the first end portion including:
    an inner, first surface,
    an outer, second surface,
    a sealing flap;
    a number of pockets on the sealing flap, the number of pockets disposed between the first end portion first surface and the first end portion second surface,
    a number of solid segments, wherein each pocket is located at a discrete location with the solid segments generally disposed about each pocket;
    each pocket includes an inner wall, an outer wall, and a plenum, the plenum disposed between the inner wall and the outer wall;
    wherein the sealing flap solid segments are unitary with each pocket inner wall and each pocket outer wall; and
    wherein the thickness of each solid segment and each pocket is generally uniform.

7. The cushion of claim 6, wherein each plenum has a thickness of between about 0.15 mm and 2.0 mm.

8. A cushion for a patient interface device, the cushion comprising:
    a first end portion structured to contact a portion of a patient's face; the first end portion has a sealing flap;
    the first end portion sealing flap includes an inner surface and an outer surface;
    a pocket including a convex wall including an inner surface and an outer surface;
    the pocket convex wall inner surface is coupled to the first end portion sealing flap outer surface;
    wherein a space is created between each pocket convex wall inner surface and the first end portion sealing flap outer surface; and
    wherein the pocket inner wall is coupled to the first end portion sealing flap outer surface.

9. A cushion for a patient interface device, the cushion comprising:
    a first end portion structured to contact a portion of a patient's face;
    the first end portion has a sealing flap;
    the first end portion sealing flap includes an inner surface and an outer surface;
    a number of pockets each including a convex wall including an inner surface and an outer surface;
    each pocket convex wall inner surface is coupled to the first end portion sealing flap outer surface;
    wherein a space is created between each pocket convex wall inner surface and the first end portion sealing flap outer surface; and
    a number of solid segments, wherein each pocket is located at a discrete location with the solid segments generally disposed about each pocket.

10. A patient interface device comprising:
    a mask including a faceplate and a cushion, the cushion comprising:

a first end portion structured to contact a portion of a patient's face;

a second end portion structured to be coupled to the faceplate;

a sidewall extending between the first end portion and the second end portion, the first end portion including a sealing flap, a first surface, a second surface, a number of pockets disposed on the sealing flap and between the first end portion first surface and the first end portion second surface, and, a number of solid segments;

wherein each pocket is located at a discrete location with the solid segments generally disposed about each pocket;

wherein the cushion second end portion is coupled to the faceplate;

each pocket including an inner wall, an outer wall, and a plenum disposed between the inner wall and the outer wall;

wherein the sealing flap solid segments are unitary with each pocket inner wall and each pocket outer wall; and wherein the thickness of each sealing flap solid segment is less than the thickness of each pocket.

11. The patient interface device of claim 10, wherein each pocket is filled with a low-viscosity medium.

12. The patient interface device of claim 11, wherein the low-viscosity medium is a medium selected from the group including air, oil, silicone fluid, or a gel.

13. The patient interface device of claim 10, wherein the first end portion includes a support flap; and the first end portion support flap at least partially overlies the first end portion sealing flap.

14. The patient interface device of claim 10 wherein: the first end portion sealing flap includes an apex region, a first side region, a second side region, a bottom region, a first transition region, and a second transition region, each side region extending from the apex region, the first transition region disposed between the first side region and the bottom region, the second transition region disposed between the second side region and the bottom region, and wherein the discrete location of a pocket is one of the apex region, the first side region, the second side region, the first transition region, or the second transition region.

15. A patient interface device comprising:
a mask including a faceplate and a cushion, the cushion comprising:
a first end portion structured to contact a portion of a patient's face;
a second end portion structured to be coupled to the faceplate;
a sidewall extending between the first end portion and the second end portion, the first end portion including a sealing flap, a first surface, a second surface, a number of pockets disposed on the sealing flap and between the first end portion first surface and the first end portion second surface, and, a number of solid segments;
wherein each pocket is located at a discrete location with the solid segments generally disposed about each pocket;
wherein the cushion second end portion is coupled to the faceplate;
each pocket including an inner wall, an outer wall, and a plenum disposed between the inner wall and the outer wall;
wherein the sealing flap solid segments are unitary with each pocket inner wall and each pocket outer wall; and
wherein the thickness of each solid segment and each pocket is generally uniform.

16. The patient interface device of claim 15, wherein each plenum has a thickness of between about 0.15 and 2.0 mm.

17. A patient interface device comprising:
a mask including a faceplate and a cushion, the cushion comprising:
a first end portion structured to contact a portion of a patient's face;
a second end portion structured to be coupled to the faceplate;
a sidewall extending between the first end portion and the second end portion;
wherein the cushion second end portion is coupled to the faceplate;
the first end portion has a sealing flap;
the first end portion sealing flap includes an inner surface and an outer surface;
a pocket including a convex wall including an inner surface, an outer surface, and a perimeter;
the pocket convex wall inner surface is coupled to the first end portion sealing flap outer surface;
wherein a space is created between each pocket convex wall inner surface and first end portion sealing flap outer surface; and
wherein the pocket inner wall is coupled to the first end portion sealing flap outer surface.

18. A patient interface device comprising:
a mask including a faceplate and a cushion, the cushion comprising:
a first end portion structured to contact a portion of a patient's face;
a second end portion structured to be coupled to the faceplate;
a sidewall extending between the first end portion and the second end portion;
wherein the cushion second end portion is coupled to the faceplate;
the first end portion has a sealing flap;
the first end portion sealing flap includes an inner surface and an outer surface;
a number of pockets each including a convex wall including an inner surface, an outer surface, and a perimeter;
each pocket convex wall inner surface is coupled to the first end portion sealing flap outer surface;
wherein a space is created between each pocket convex wall inner surface and first end portion sealing flap outer surface; and
a number of solid segments, wherein each pocket is located at a discrete location with the solid segments generally disposed about each pocket.

* * * * *